United States Patent [19]

Brohammer et al.

[11] Patent Number: 5,653,702
[45] Date of Patent: Aug. 5, 1997

[54] ABSORBENT BODY IN AN ABSORBENT ARTICLE, SUCH AS A SANITARY NAPKIN, A PANTY PROTECTOR, INCONTINENCE GUARD, DIAPER AND THE LIKE

[75] Inventors: Göran Brohammer, Billdal; Berit Rosseland, Lindome; Magnus Qvist, Floda; Berith Porsö, Partille, all of Sweden

[73] Assignee: Molnlycke AB, Gothenburg, Sweden

[21] Appl. No.: 318,838

[22] PCT Filed: Apr. 21, 1993

[86] PCT No.: PCT/SE93/00347

§ 371 Date: Oct. 18, 1994

§ 102(e) Date: Oct. 18, 1994

[87] PCT Pub. No.: WO93/21881

PCT Pub. Date: Nov. 11, 1993

[30] Foreign Application Priority Data

Apr. 28, 1992 [SE] Sweden .................... 9201332

[51] Int. Cl.⁶ .................................................. A61F 13/15
[52] U.S. Cl. ................................. 604/370; 604/378
[58] Field of Search .................... 604/365–366, 604/370, 378–380

[56] References Cited

U.S. PATENT DOCUMENTS

| | | | |
|---|---|---|---|
| 3,616,797 | 11/1971 | Champaigng, Jr. et al. | 604/365 |
| 4,676,786 | 6/1987 | Nishino | 604/378 |
| 4,737,404 | 4/1988 | Jackson . | |
| 4,761,322 | 8/1988 | Raley | 428/198 |
| 4,872,870 | 10/1989 | Jackson | 604/366 |
| 4,988,345 | 1/1991 | Reising | 604/368 |
| 5,019,063 | 5/1991 | Marsan et al. | 604/368 |
| 5,057,166 | 10/1991 | Young, Sr. et al. | 156/62.2 |
| 5,300,054 | 4/1994 | Feist et al. | 604/378 |
| 5,360,420 | 11/1994 | Cook et al. | 604/378 |
| 5,411,497 | 5/1995 | Tanzer et al. | 604/368 |
| 5,439,458 | 8/1995 | Noel et al. | 604/378 |

FOREIGN PATENT DOCUMENTS

| | | |
|---|---|---|
| 202472A1 | 11/1986 | European Pat. Off. . |
| 0209775A1 | 1/1987 | European Pat. Off. . |
| 0462620A1 | 12/1991 | European Pat. Off. . |
| 465806 | 11/1991 | Sweden . |
| WO91/10413 | 7/1991 | WIPO . |
| 9114415A1 | 10/1991 | WIPO . |

*Primary Examiner*—Michael J. Milano
*Attorney, Agent, or Firm*—Burns, Doane, Swecker & Mathis LLP

[57] ABSTRACT

An absorbent body in an absorbent article, such as a sanitary napkin, panty protector, incontinence guard, diaper or the like. The absorbent body includes a first layer, an admission layer (4), which comprises a mixture of 80–95% resilient fibres and 5–20% heat-actuable binding fibres, preferably bicomponent fibres, and a second layer, a storage and dispersion layer (5), which comprises a mixture of 45–90% absorbent fibres and 5–15% heat-actuable binding fibres, wherein the binding fibres are heat treated so as to bond together and to hold the fibre structures together in the first and second layers (4, 5), such that these layers will form a laminate that has a tensile strength of at least 2N/50 mm in a dry state. The absorbent body also has a high surface dryness and low rewetting tendency and exhibits good absorption properties.

15 Claims, 1 Drawing Sheet

ABSORBENT BODY IN AN ABSORBENT ARTICLE, SUCH AS A SANITARY NAPKIN, A PANTY PROTECTOR, INCONTINENCE GUARD, DIAPER AND THE LIKE

The present invention relates to an absorbent body in an absorbent article, such as a sanitary napkin, panty protector, incontinence guard, diaper and like articles.

BACKGROUND ART

Many different designs of absorbent articles of this kind are known to the art. The absorbent body of products of this nature are normally comprised of one or more layers of cellulose fluff pulp, which is sometimes intermixed with so-called superabsorbents, which are polymers that are capable of absorbing water or body liquid in quantities equal to several times their own weight. The absorbent body may also include other constituents, for instance constituents which improve the liquid-dispersing properties or the ability of the body to remain intact and also its ability to resist deformation in use.

SE-B-465 806 describes an absorbent body for use in absorbent articles of this kind, said absorbent body including a first layer which is intended to lie proximal to the wearer in use and which includes a first mixture of fibres, and a second layer which includes a second mixture including absorbent fibres.

One serious problem with articles of this kind is that they often begin to leak long before their total absorption capacity has been fully utilized. This is due, among other things, because the body liquid discharged by the wearer is unable to penetrate into the absorbent material quickly enough and, instead, leaks from the sides of the sanitary napkin or incontinence guard.

Another problem relates to so-called rewetting, which means that absorbed body liquid is pressed back into contact with the wearer's skin by external forces, for instance when the wearer sits down.

It is desirable for the surface of the article which faces towards the wearer in use, i.e. the proximal surface, remains as dry as possible. This is difficult to achieve, particularly with sanitary napkins, since the menstruation liquid has a high viscosity and therefore tends to fasten to the surface material of the napkin.

A thin article is also desired, so that the article can be worn as discretely as possible.

OBJECTS AND SUMMARY

An object of the present invention is to provide an absorbent article of the kind defined in the introduction which can be made very thin while still being essentially proof against leakage. The article shall also exhibit high surface dryness and low rewetting tendencies. Another object is to provide an article in which the absorbent material has a high tensile strength which corresponds at least 2N/50 mm in a dry state, so that said material can be handled in the form of rolls.

These objects are achieved in accordance with the present invention by providing the absorbent article with an absorbent body which includes a first layer which is intended to lie proximal to the wearer in use and which includes a first mixture fibres, and a second layer which includes a second mixture including absorbent fibres, said absorbent body being characterized in that said first mixture is 80-95 percent by weight resilient fibres and 5-20 percent by weight heat-actuable binding fibres, said heat-actuable fibres being actuable at temperatures at which the resilient fibres are not heat-actuable; said second mixture is 45-90 percent by weight absorbent fibres and 5-15 percent by weight, preferably 8-10 percent by weight heat-actuable binding fibres; and in that the binding fibres have been bonded together by heat treatment and function to hold the fibre structures together in said layers such that said layers form a laminate having a tensile strength of at least 2N/50 mm in a dry state.

The second layer may also include superabsorbent material, which is either admixed with the fibres or is applied in the form of one or more layers between the fibre layers. Alternatively, superabsorbent material can be applied in the form of a laminate between tissue layers.

The combination of two absorbent layers in the aforesaid manner provides the advantage of having a first admission layer which is able to quickly take-up a given quantity of liquid and allow the liquid to drain readily to an underlying layer which absorbs and disperses or spreads the liquid. The upper layer, the admission layer, is thus drained so as to reduce rewetting tendencies to a low level and to provide a high degree of surface dryness. The lower layer, the liquid storage layer, is constructed so that the liquid will be spread over essentially the whole of the layer, such as to utilize the absorbent capacity of the article in an effective manner.

The invention also relates to a method of manufacturing the absorbent material, in which a fibre web is dry-formed on top of a similarly dry-formed fibre web, wherein one of the fibre webs includes a mixture of 80-95 percent by weight resilient fibres and 5-20 percent by weight heat-actuable binding fibres, and wherein the other fibre web includes a mixture of 45-90 percent by weight absorbent fibres and 5-15 percent by weight heat-actuable binding fibres, and wherein the mutually superimposed fibre webs are heated so as to activate the binding fibres and to thermally bond said fibre webs together, whereafter the webs are compressed to form a laminate structure having a tensile strength of at least 2N/50 mm in a dry state.

BRIEF DESCRIPTION OF THE DRAWINGS

The invention will now be described in more detail with reference to two exemplifying embodiments thereof and also with reference to the accompanying drawing.

DESCRIPTION OF EXEMPLIFYING EMBODIMENTS

Figure 1:
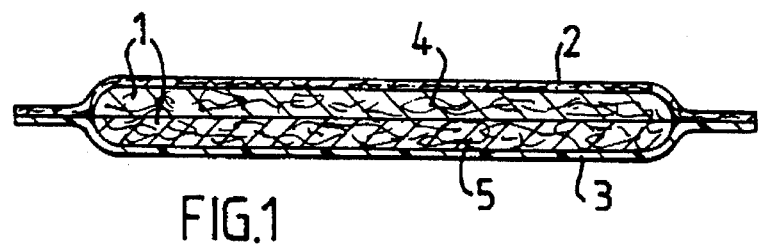
FIG. 1 is a schematic, cross-sectional view of one embodiment of an inventive sanitary napkin.

FIG. 1 illustrates a sanitary napkin constructed in accordance with one embodiment of the invention. The sanitary napkin includes conventionally an absorbent body 1 which is enclosed between a liquid-permeable top sheet 2, which conveniently consists of soft non-woven material, a perforated plastic film or the like and which lies proximal to the wearer in use, and a liquid-impermeable bottom sheet 3. The sheets 2, 3 have parts which extend beyond the absorbent body 1 and are joined together at these protruding parts. The bottom sheet 3 is comprised of a suitable plastic material, for instance polyethylene plastic. Naturally, the top and bottom sheets may be formed from other known materials, within the scope of the invention.

The absorbent body 1 includes two layers, an upper liquid-admission layer 4 and a lower liquid-dispersing and storing layer 5. The function of the admission layer 4 is to quickly receive a given quantity of liquid. The liquid is intended to be held loosely in the fibre structure and to drain rapidly therefrom. Accordingly, the admission layer 4 has a resilient or springy and preferably non-absorbent fibre structure which is comprised of a mixture of 80–95 percent by weight hydrophilic synthetic fibres, for instance polyester, polypropylene, polyacryl, polyamide fibres having a thickness of 0.4–0.9 g/km (4–9 dtex) and a length of 3–6 mm, and 5–20 percent by weight binding fibres, preferably thermoplastic fibres of the type bicomponent fibres having a poly-olefin core, e.g. polypropylene or polyester core, and a polyolefin casing, e.g. a polyethylene casing, whose melting point is lower than the melting point of the core material. The bicomponent fibres will preferably have a thickness of 0.22–0.33 g/km (2.2–3.3 dtex) and a fibre length of 3–6 mm. The admission layer may also be comprised of resilient absorbent fibres, such as chemi-thermomechanical pulp (CTMP), or chemically stiffened cellulose fibres which will not collapse when wetted but will retain an open structure of large pore volume. These fibres constitute 80–95 percent by weight of the fibre structure, which also includes 5–20 percent by weight binding fibres of the aforesaid kind.

The material is bonded together by heating the material to a temperature above the melting point of the bicomponent-fibre casing material but lower than the melting point of the bicomponent-fibre core material and the melting point of the resilient fibres. In this way, there is obtained a bonded fibre structure, although with relatively weak bonds, such as to enable the material to swell when wetted and to receive the desired amount of liquid.

The high percentage of resilient fibres in the admission layer 4 prevents the material from collapsing when wetted and is, instead, active in holding the capillaries of the fibre structure open. Furthermore, the material retains its bulk and resiliency, for instance after being compressed in a packaging machine or by virtue of the weight of the user. The admission layer 4 will preferably have a bulk of between 8–30 cm$^3$/g.

As before mentioned, the admission layer 4 is intended to enable the liquid received to drain quickly to the underlying storage-and-dispersing layer 5, which is intended to spread the liquid over a wide surface area and to retain the liquid. Thus, this layer will preferably have a fibre structure which has a fine capillary system. The layer includes between 45–90 percent by weight absorbent fibres, e.g. pulp, cotton or viscose fibres, and between 5–15 percent by weight, and preferably between 8–10 percent by weight binding fibres, suitably bicomponent thermoplastic fibres of a kind corresponding to the bicomponent fibres in the admission layer 4. The layer will also preferably include superabsorbent material, i.e. polymers that are capable of absorbing water and body liquid in quantities corresponding to several times their own weight. The superabsorbent material will preferably be present in an amount corresponding to 5–30 percent by weight, calculated on the dry weight of the layer.

The dispersion layer 5 is thermally bonded by heating the layer to a temperature between the respective melting points of the bicomponent-fibre casing and core materials, in a manner corresponding to the admission layer 4. The bonds in the fibre structure are relatively weak, with bonding points located solely between the binding fibres, which thus form a three-dimensional network structure with free spaces for the absorbent fibres and superabsorbent material, when present. When the layer becomes wet, the superabsorbent particles are able to swell and to break the bonds. This eliminates or at least reduces, the otherwise usual negative effect that the thermobonding of absorbent material often has on the absorption capacity. Bonding of the structure is primarily desirable in the dry product in conjunction with its manufacture and also in conjunction with other article-handling processes prior to its use.

The liquid storage-and-dispersing layer 5 may conveniently be provided with a compression pattern, so as to increase dispersion of liquid in the longitudinal direction of the sanitary napkin. For instance, this pattern may have the form of longitudinally extending bands or stripes which, because of their greater compression, have finer capillaries than the surrounding absorbent material. The absorbed body liquid will therefore be dispersed more quickly along the compressed bands than through the surrounding material. By dispersing liquid in the longitudinal direction of the layer 5 in this manner, absorbent material which is located far from the so-called wetting point will be utilized.

Figure 2:
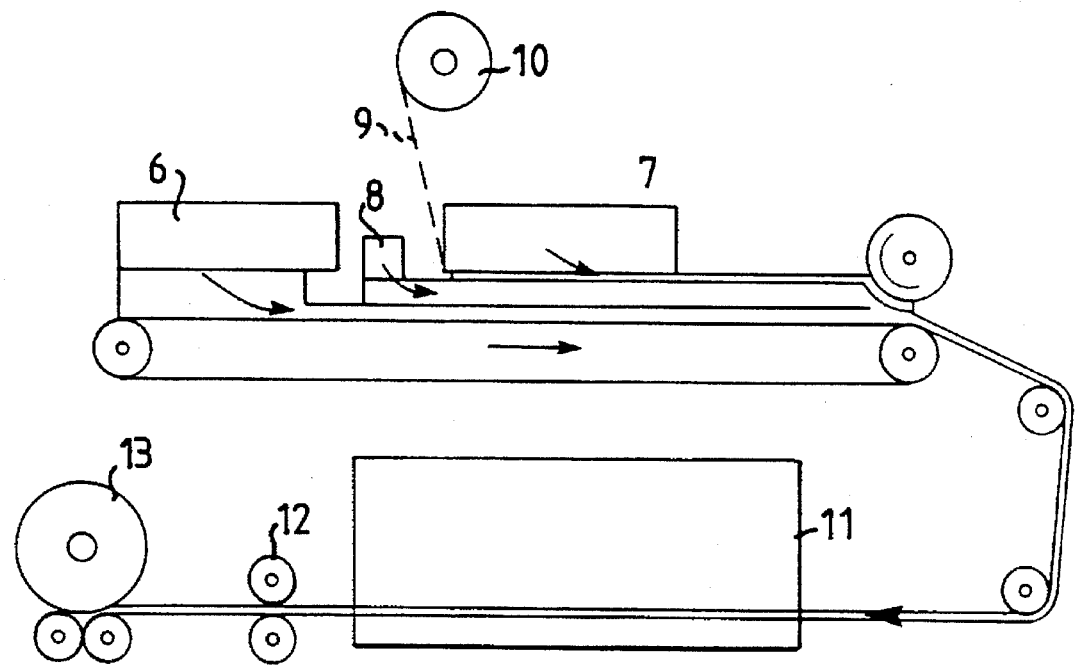
FIG. 2 illustrates schematically an arrangement of apparatus for producing the sanitary napkin illustrated in FIG. 1.

FIG. 2 illustrates a method of manufacturing the inventive absorbent material. In accordance with a dry-forming process, a web comprising a first fibre mixture and intended to form the admission layer 4 is formed in a first forming head 6. Similarly, a web comprising a second fibre mixture and intended to form the liquid dispersing-and-storing layer 5 is formed in a second forming head 7 and laid on top of the first fibre mixture. The superabsorbent is applied on top of the second fibre mixture 5, suitably in the form of a tissue-superabsorbent-laminate. This laminate may be produced, for instance, by applying superabsorbent onto a tissue electrostatically, subsequent to having sprayed a thin layer of melt glue onto the tissue layer. A second tissue layer is laid on top of the superabsorbent layer. The resultant superabsorbent-tissue-laminate 9 can be readily handled and may, for instance, be reeled onto a reel 10. Alternatively, superabsorbent is strewn out in the fibre mixture through the agency of a metering device 8.

Naturally, the fibre mixture which is to form the dispersing-and-storing layer 5 may be formed into a web in the first forming head 6, and the fibre mixture which is to form the admission layer 4 may be formed into a web on top of the liquid dispersing-and-storing layer through the agency of the second forming head 7.

The thus combined layers are then passed through an oven 11 in which thermobonding of the material takes place, whereafter the composite web is calendared in a calendar 12 and rolled-up on a take-up reel 13.

The composite laminate structure is sufficiently strong to be handled as roll material, i.e. has a tensile strength equal to or greater than 2N/50 mm.

Instead of using the aforedescribed superabsorbent-tissue-laminate 9, superabsorbent can be mixed with the fibres in the storing-and-dispersing layer 5 or may be applied in the form of one or more layers between fibre layers. The application of superabsorbent in the form of a layer or coating has certain advantages over the admixture of superabsorbent with the fibres. Among other things, a superabsorbent layer or coating will improve dispersion of the liquid, will reduce rewetting tendencies, and will improve the coherency of the article, this latter property being a measurement of the ability of the absorbent body to retain liquid under load.

Alternatively, the superabsorbent material can be totally excluded from the storing-and-dispersing layer.

Figure 3:
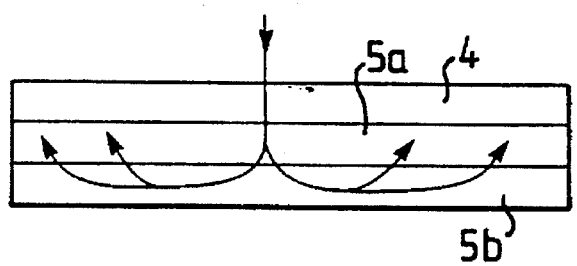
FIG. 3 is a schematic cross-sectional view of one alternative embodiment of an inventive absorbent body.

FIG. 3 illustrates a further alternative in which the liquid storing-and-dispersing layer 5 is divided into two storingand-dispersing layers 5a and 5b respectively. In this case, the superabsorbent material is applied in the storing layer 5a, which is located nearest the admission layer 4, while the dispersing layer 5b is located at the bottom, nearest the bottom sheet 3.

The composition of the storing layer 5a will preferably be: 45–70 percent by weight absorbent fibres, 5–15 percent by weight binding fibres and 5–30 percent by weight superabsorbents material, while the dispersing layer 5b will preferably have the following composition: 80–90 percent by weight absorbent fibres and 10–20 percent by weight binding fibres.

An absorbent body constructed in this way would function in the following manner. Liquid is absorbed instantaneously in and passes through the admission layer 4, whereafter the liquid penetrates the storing layer 5a and is absorbed therein, where the liquid collects and is dispersed throughout the dispersing layer 5b. When the superabsorbent material in the storing layer 5a has drained the capillary system of said layer, liquid is able to spread back to the storing layer 5a from the dispersing layer 5b. In order for a transfer of liquid to take place between the storing-and-dispersing layers in both directions, it is necessary for the capillarity and thickness of the layers to be correctly balanced.

It will be understood that the invention is not restricted to the illustrated and described exemplifying embodiments thereof and that the invention is not limited solely to sanitary napkins. For instance, the absorbent body can be used to absorb urine in incontinence guards and diapers.

We claim:

1. An absorbent body, comprising:
   a first layer which is intended to lie proximal to a wearer in use and which includes a first mixture of fibres, and
   a second layer which includes a second mixture including absorbent fibres,
   said first mixture is 80–95 percent by weight resilient fibres and 5–20 percent by weight heat-actuable binding fibres, said heat-actuable binding fibres being actuable at temperatures at which the resilient fibres are not heat-actuable,
   said second mixture is 45–90 percent by weight absorbent fibres and 5–15 percent by weight, heat-actuable binding fibres,
   the heat-actuable binding fibres have been bonded together by heat treatment and include means for holding the fibres together in said layers such that said layers are thermally bonded together to form a laminate, wherein the layers, without any top or bottom cover sheets, provide a tensile strength of at least 2N/50 mm in a dry state.

2. An absorbent body according to claim 1, wherein the resilient fibres are comprised of hydrophilic synthetic fibres.

3. An absorbent body according to claim 1, wherein the resilient fibres are comprised of wet-stable absorbent fibres.

4. An absorbent body according to claim 1, wherein the binding fibres are comprised of bicomponent fibres having a fibre core material and a casing material that has a lower melting point than the fibre core material; and the heat treatment of the absorbent body has been carried out at a temperature which is lower than the core material melting point but higher than the casing material melting point.

5. An absorbent body according to claim 4, wherein bonds between the binding fibres are so weak that when the absorbent body is wetted the absorbent body swells and breaks said bonds.

6. An absorbent body according to claim 1, wherein the second layer includes 5–30 percent by weight of a superabsorbent material, calculated on the dry weight of the layer.

7. An absorbent body according to claim 6, wherein the superabsorbent material is present in at least one layer disposed between layers of the fibres of the second layer.

8. An absorbent body according to claim 7, wherein the superabsorbent material is disposed between layers of tissue.

9. An absorbent body according to claim 1, wherein the second layer exhibits a compression pattern which functions to increase dispersion of liquid in a longitudinal direction of the absorbent body, said compression pattern having a form of longitudinally extending compressed bands.

10. An absorbent body according to claim 1, wherein the said second layer is divided into two layers, a storage layer and a dispersion layer; and the storage layer includes 45–70 percent by weight absorbent fibres, 5–15 percent by weight heat-actuable binding fibres and 5–30 percent by weight superabsorbent material and the dispersion layer includes 80–90 percent by weight absorbent fibres and 10–20 percent by weight heat-actuable binding fibres.

11. A method of manufacturing a web of absorbent material intended for an absorbent article, such as a sanitary napkin, panty protector, incontinence guard, diaper and like article in accordance with claim 1, comprising the steps of:
   dry-forming a fibre web on top of another similarly dry-formed fibre web, wherein one of the fibre webs includes a mixture of 80–95 percent by weight resilient fibres and 5–20 percent heat-actuable binding fibres and the other of said fibre webs includes a mixture of 45–90 percent by weight absorbent fibres and 5–15 percent by weight heat-actuable binding fibres;
   heating the mutually superimposed fibre webs so as to activate the binding fibres and thermally bond said fibre webs to each other, and
   compressing the fibre webs to form a laminate having a tensile strength of at least 2N/50 mm in a dry state.

12. A method according to claim 11, further comprising the step of superabsorbent material in or on the other of said fibre webs in conjunction with dry-forming said web.

13. An absorbent body according to claim 1, wherein the second mixture includes 8–10% heat actuable binding fibres.

14. An absorbent body according to claim 3, wherein the resilient fibres are chemically stiffened cellulose fibres.

15. An absorbent body according to claim 3, wherein the resilient fibres are chemi-thermomechanical pulp.

* * * * *